(12) United States Patent
Kirk et al.

(10) Patent No.: US 7,300,461 B2
(45) Date of Patent: Nov. 27, 2007

(54) INTRAVASCULAR STENT WITH EXPANDABLE COATING

(75) Inventors: Matthew P. Kirk, Pendleton, NY (US); Chandra Venkatraman, Amherst, NY (US)

(73) Assignee: Blue Medical Devices B.V., Helmond HN (NL)

( * ) Notice: Subject to any disclaimer, the term of this patent is extended or adjusted under 35 U.S.C. 154(b) by 579 days.

(21) Appl. No.: 10/333,975

(22) PCT Filed: Jul. 17, 2001

(86) PCT No.: PCT/EP01/08282

§ 371 (c)(1),
(2), (4) Date: Feb. 27, 2003

(87) PCT Pub. No.: WO02/09791

PCT Pub. Date: Feb. 7, 2002

(65) Prior Publication Data

US 2003/0187496 A1  Oct. 2, 2003

Related U.S. Application Data

(60) Provisional application No. 60/221,633, filed on Jul. 28, 2000.

(51) Int. Cl.
*A61F 2/06* (2006.01)
(52) U.S. Cl. .................. 623/1.46; 427/2.24
(58) Field of Classification Search ........... 623/1.15, 623/1.44, 1.46, 1.47; 606/191–198; 523/423, 523/149, 407, 63, 71; 427/2.24; 424/422
See application file for complete search history.

(56) References Cited

U.S. PATENT DOCUMENTS 6,248,811 B1 * 6/2001 Ottersbach et al. ......... 523/423

FOREIGN PATENT DOCUMENTS

| WO | WO 96/39943 A1 | 12/1996 |
|---|---|---|
| WO | WO 97/40207 A1 | 10/1997 |
| WO | WO 99/62572 A1 | 12/1999 |
| WO | WO 99/64085 A1 | 12/1999 |

OTHER PUBLICATIONS

D. Neerinck et al., "Diamond-like Nanocomposite Coatings for Low-Wear and Low Friction Applications in Humid Environments", Preparation and Characterization, Elsevier Sequoia, NL, vol. 317, No. 1-2, Apr. 1, 1998, pp. 402-404.
C. Venkatraman et al., "Electrical Properties of Diamond-like Nanocomposite Coatings", Thin Solid Films, Elsevier-Sequoia S.A., vol. 308-309, No. 1-4, Oct. 31, 1997, pp. 173-177.
B. Dorfman et al., "Diamond-like Nanocomposite Coatings: Novel Thin Films", Advances in Science and Technology New Diamond and Diamond-Like Films, vol. 6, 1995, pp. 219-226.

* cited by examiner

*Primary Examiner*—Kevin T. Truong
(74) *Attorney, Agent, or Firm*—Foley & Lardner LLP

(57) ABSTRACT

An intravascular stent (26) has a surface coated with a biocompatible layer. The layer contains a diamond like nanocomposite material. This nanocomposite material comprises carbon, hydrogen, silicon and oxygen as constituent elements. The layer has a stress which is less than 150 MPa in order to ensure a high degree of flexibility and a complete expandability. This lower stress is obtained by the inclusion of relatively large amounts of Si:O bonds. In a preferable embodiment the layer with diamond like nanocomposite material covers the stent (26) for 100%. This is obtained by allowing the stent to move freely along a wire during CAVD deposition.

8 Claims, 1 Drawing Sheet

INTRAVASCULAR STENT WITH EXPANDABLE COATING

FIELD OF THE INVENTION

The present invention relates to an intravascular stent having a surface coated with a biocompatible layer.

BACKGROUND OF THE INVENTION

Intravascular stents are known in the art. These stents can be tubular in form. Numerous tubular stent designs are now on the market. Many of them comprise a radially expandable mesh type metal network, either in the form of a fine wire mesh or of a tube wall wherein a recurring pattern of holes have been cut (e.g. by means of a laser) in order to form a so-called slotted tube stent. Stents can also have an expandable tubular spring like structure such as a so-called coil stent or a so-called ring stent.

A stent may be introduced into an artery according to following method. Protected by a sheath the stent is advanced across the lesion in the artery. Once in position the sheath is removed from the stent. By means of a balloon catheter the stent is radially fully expanded. Thereafter the catheter is withdrawn. So a stent must be flexible enough to pass through the vasculature without causing damage. The stent must be strong enough to support a diseased vessel and the stent must survive crimping onto a catheter followed by radial expansion without breaking or weakening. These severe requirements often lead to the choice of metal as material for the stents. The metal is preferably stainless steel, titanium, tantalum, platinum, nitinol or a nickel-titanium alloy.

However, metals in general, and stainless steel in particular, tend to be thrombogenic, i.e. metals encourage the formation of blood clots. Metal stents also cause neointimal hyperplasia. This is one of the reasons why the surfaces of prior art stents have been provided with a biocompatible layer.

WO-A-99/62572 of applicant discloses an intravascular metal stent a major part of the surface of which has been coated with a biocompatible layer containing a diamond like nanocomposite material.

Although showing a substantial reduction in thrombogenecity and neointimal hyperplasia, metal may still be present on the surface after the above-mentioned crimping followed by an expansion of the stent. This may lead to adverse tissue reactions.

SUMMARY OF THE INVENTION

It is an object of the present invention to provide a stent coated with a layer having an increased flexibility and expandability. It is another object of the present invention to provide a stent with a one hundred per cent coating coverage.

According to the invention there is provided an intravascular stent having a surface coated with a biocompatible layer. The layer contains a diamond like nanocomposite material. The nanocomposite material comprises carbon, hydrogen, silicon and oxygen as constituent elements. The layer has a stress which is less than 150 MPa, preferably less than 120 MPa, and most preferably less than 100 MPa in order to ensure a complete expandability and flexibility of the layer even after crimping on the catheter and after expansion from the catheter.

The nanocomposite material preferably comprises a network of a-C:H interpenetrating with a network of a-Si:O.

Silicon is preferably present in an amount ranging from 10 to 40%. Oxygen is preferably present in an amount ranging from 8 to 40%.

The layer is preferably deposited by means of a plasma assisted chemical vapour deposition (PACVD) method. A siloxane precursor material is evaporated and drawn into vacuum where the vapor is fragmented and ionized. This siloxane precursor gives the constituent elements of carbon, hydrogen, silicon and oxygen in the layer. Preferably, the siloxane precursor is chosen from the group consisting of hexamethyldisiloxane, octamethylcyclotetrasiloxane and tetramethyldisiloxane. These type of precursors give—possibly in combination with the addition of oxygen to the vapours—large amounts of Si—O bonds in the deposited nanocomposite material and this is believed to give the low stress values and to give an increased flexibility and expandability to the layer.

According to a preferable embodiment of the invention, the layer with the nanocomposite material covers hundred per cent (100%) of the surface. Most preferably, the layer has a minimum thickness of 50 nanometer (nm). This 100% coverage is may be obtained by means of a particular way of fixing the stents during the PACVD method, as will be explained hereinafter.

The 100% coverage together with the high degree of flexibility and expandability substantially reduce the likelihood that the layer will crack or spall during the mechanical deformations of the stent and substantially reduce the likelihood that metal ions are leached out and result in adverse tissue reaction.

BRIEF DESCRIPTION OF THE DRAWINGS

The invention will now be described into more detail with reference to the accompanying drawings wherein.

DESCRIPTION OF THE PREFERRED EMBODIMENTS OF THE INVENTION

Figure 1:
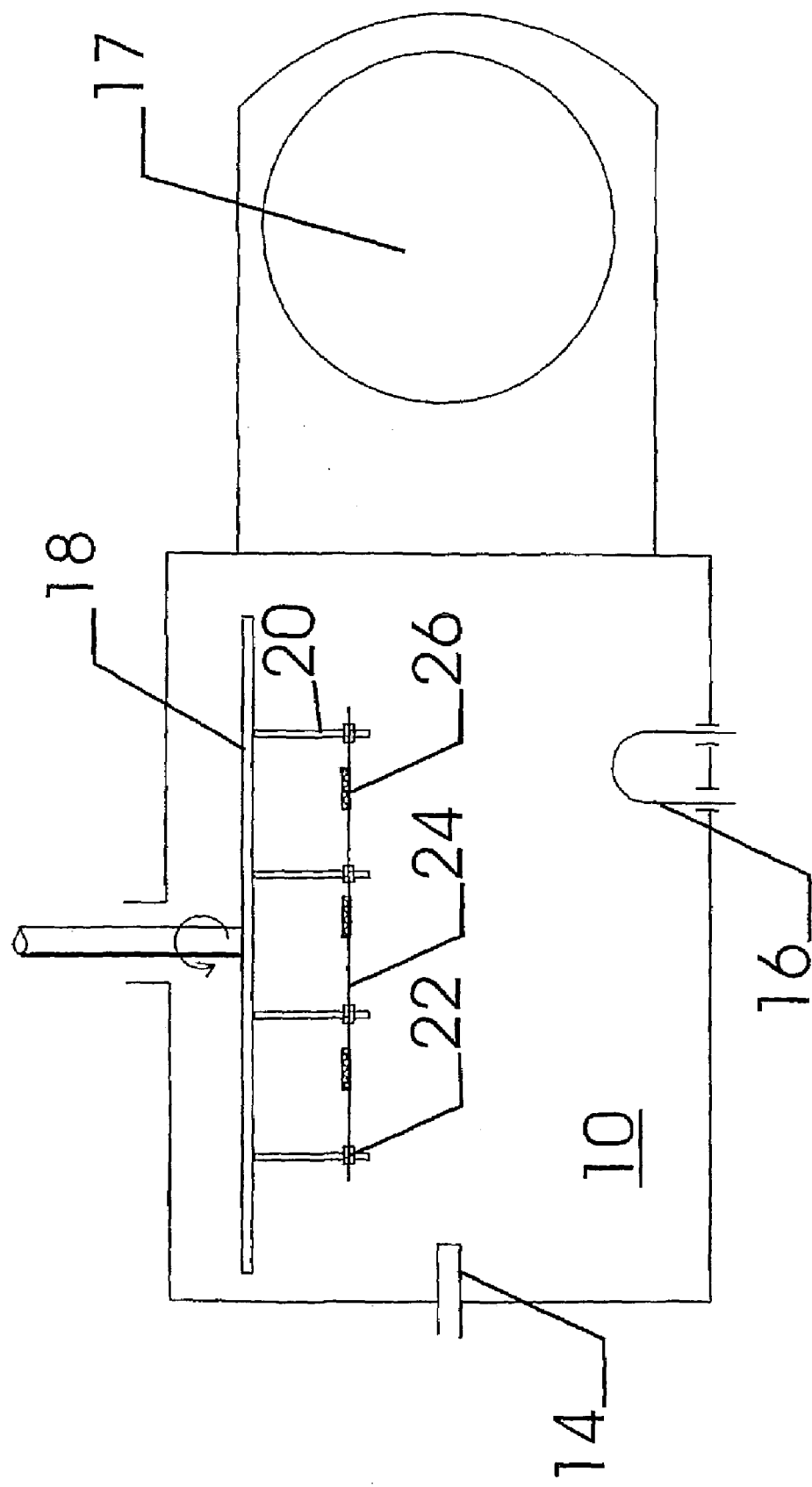
FIG. 1 is a upper view diagram detailing a PACVD method for coating a stent according to the invention.

FIG. 1 shows the main components required for carrying out a PACVD method for coating a stent according to the invention. 10 is the vacuum deposition chamber, 12 is the plasma generation chamber, 14 is an inlet for siloxane vapour, 16 is a resistively heated tungsten electrode, 17 is a vacuum pomp valve and 18 is rotating platen. Rods or posts 20 are fixed to the platen 18. The rods 20 contain threaded nuts 22. The threaded nuts 22 clamp a stainless steel wire 24 with a diameter of about 0.13 mm. The distance between the steel wire 24 and the platen 18 is about 3 cm. Stents 26 are suspended on the steel wire 24. Multiple stents 26 can be coated in this way by using one piece of steel wire 24 for each stent 26 and a pair of rods 20, one at each end of the stent 26.

The siloxane precursor material is evaporated outside the vacuum chamber and the siloxane vapour is drawn into the vacuum chamber 10 through the inlet 14. The fragmented ions and radicals are deposited on the stent 26 with simultaneous argon ion bombardment resulting in an amorphous diamond like nanocomposite layer. A low energy argon plasma cleaning of parts of the stent is accomplished through biasing of the stents 26 with a low frequency RF bias before depositing the film. This is done to improve the adhesion. The RF bias is then turned off during the carbon film deposition. Typical deposition parameters are as follows:

vacuum pressure: $8.10^{-4}$ to $30.10^{-4}$ Torr
RF bias: 0 to 100 Volt
Deposition time 10 to 15 minutes Precursor type: hexamethyldisiloxane (invention stent) and 2,3,4 triphenyl-nonamethyl-pentasiloxane (prior art stent)

Siloxane liquid flow: 0.05 to 0.13 grams per minute

Argon flow: 12 to 21 sccm

The stent 26 can move freely along the axis of steel wire 24 during deposition as the platen 18 rotates at a speed of about 7 rotations per minute. As a result the stent 26 is not hold in a static position. This results in a 100% coverage of the surface of stent 26.

From a broader perspective, every deposition method where the stent 26 is not held statically in a fixed position, is suitable. Such a deposition method could be realized, e.g. by holding the stent fixed at predetermined spots during a partial period of the deposition time and holding the stent fixed at other predetermined spots during other periods of the deposition time.

To determine whether the stents 26 have been coated on the complete surface (100% coverage), optical microscopy was utilized to determine if coloration was present. It is hereby understood that coloration indicates the presence of a coating. With a deposition method as illustrated hereabove in FIG. 1, coloration was observed on both the radially inside and outside surfaces of the stent. This is in contrast to the teaching that during deposition the metal stent 26 would form a so-called Faraday screen which would prevent the plasmas from entering the inside of the stent and would prevent the radially inside surface from being coated.

In order to test the flexibility of the deposited layer a balloon catheter was used to expand the stents from a 1.5-mm to 2.5-mm diameter. This test simulates the conditions that a coated stent would undergo when inserted inside an artery. A scanning electron microscope was used to observe any cracking or delamination of the coating before and after the stent expansion.

Prior art.

When coating the stents as in the prior art, using a pentasiloxane type precursor and RF biasing varying from 0 to 100 V on the samples, it was quickly demonstrated that the coatings deposited using the pentasiloxane precursor under different depositions conditions resulted in films that exhibited large amount of spalling and delamination of the coating after expansion. This spalling and delamination increases the risk for leaching of metal ions and the risk for thrombogenic reactions and for neointimal hyperplasia. Film properties of the deposited diamond like carbon nanocomposite layer have been measured on control samples which were included in the depositions. Table 1 hereunder gives a range of measured values. Thickness values were measured on flat witness coupons placed at the same elevation as the stent during the deposition. Hardness measurements were performed using nanoindentation on witness coupons. Stress measurements were taken on Silicon wafers using the Stoney Method. This method is disclosed in G. G. Stoney, "The Tension of Metallic Films Deposited by Electrolysis", Proceedings of the Royal Society of London, A82, 1909, p172-175.

TABLE 1

Prior art: Properties of expandable carbon based film using pentasiloxane precursor.

| Film Property | Range |
| --- | --- |
| thickness | 160 nm to 670 nm |
| hardness | 3 Gpa to 8 GPa |
| stress | 180 MPa-260 MPa |
| Si content | 10-30% |
| O content | 5-20% |

Invention

When using an alternative precursor such that it had a larger number of Si—O bonds than the pentasiloxane precursor material, it was believed by the inventors that increased Si:O bonding could result in a more flexible film. This is because increasing the Si—O content in carbon based hard films results in lower film stress. It was also believed that this lower stress was essential in making films expandable and flexible. A hexamethyldisiloxane precursor was utilized to achieve the higher Si—O content film. Film properties such as hardness, thickness and film stress were measured on control samples that were included in the depositions. Table 2 below gives a range of measured values for this particular coating.

TABLE 2

Invention: Thickness, Hardness and Stress of expandable carbon based film (invention)

| Film Property | Range |
| --- | --- |
| Thickness | 80 to 120 nm |
| Hardness | 3 to 6 Gpa |
| Stress | <100 MPa |
| Si content | 10-40% |
| O content | 8-40% |

Next to a hexamethyldisiloxane precursor other precursors may also be used, such as octamethylcyclotetrasiloxane and tetramethyldisiloxane. The addition of $O_2$ to these vapours during the PACVD process will also increase the amount of Si—O bonding.

By utilizing specific coating parameters and fixturing techniques, stents were successfully coated with a flexible and fully encapsulating film. The advantage of these carbon based films over traditional diamond like carbon films is the inclusion of large amounts Si:O bonds which are responsible for the improved flexibility, expandability and lower stress of the applied coating. Because of these characteristics, coating adhesion to the stent is excellent even after stent expansion by almost 100%. By optimizing deposition conditions it was possible to produce a hard, low stress film which could potentially be used in stent or other related bio-medical applications.

The invention claimed is:

1. An intravascular stent comprising a surface coated with a biocompatible layer, said layer comprising a diamond-like nanocomposite material, said nanocomposite material comprising carbon, hydrogen, silicon and oxygen as constituent elements, said layer having a stress less than 150 MPa;

wherein silicon is present in an amount ranging from 10 to 40%, wherein oxygen is present in an amount ranging from 8 to 40%, and wherein the carbon, the hydrogen, the silicon and the oxygen are obtained from decomposition of a precursor, said precursor being selected from the group consisting of hexamethyldisiloxane, octamethylcyclotetrasiloxane and tetramethyldisiloxane.

2. A stent according to claim 1 wherein said stress is less than 100 MPa.

3. A stent according to claim 1, wherein said nanocomposite material comprises a network of a-C:H interpenetrating with a network of a-Si:O.

4. A stent according to claim 1, wherein silicon is present in the layer in an amount ranging from 10 to 40%.

5. A stent according to claim 1, wherein oxygen is present in the layer in an amount ranging from 8 to 40%.

6. A stent according to claim 1, wherein carbon, the hydrogen, the silicon and the oxygen are obtained from decomposition of a precursor, said precursor being selected from the group consisting of hexamethyldisiloxane, octamethylcyclotetrasiloxane and tetramethyldisiloxane.

7. A stent according to claim 1, wherein said layer covers one hundred per cent of the surface.

8. A stent according to claim 1 wherein said layer has a minimum thickness of 50 nm.

* * * * *